United States Patent
Hygelund et al.

(10) Patent No.: US 10,722,102 B2
(45) Date of Patent: Jul. 28, 2020

(54) ENDOSCOPE FIELD STOP ENCODING SYSTEM AND METHOD

(71) Applicant: ARTHREX, INC., Naples, FL (US)

(72) Inventors: John Hygelund, Santa Barbara, CA (US); David D'Alfonso, Gaviola, CA (US); Bruce Laurence Kennedy, Santa Barbara, CA (US)

(73) Assignee: ARTHREX, INC., Naples, FL (US)

( * ) Notice: Subject to any disclaimer, the term of this patent is extended or adjusted under 35 U.S.C. 154(b) by 375 days.

(21) Appl. No.: 15/695,997

(22) Filed: Sep. 5, 2017

(65) Prior Publication Data

US 2019/0069760 A1 Mar. 7, 2019

(51) Int. Cl.
*A61B 1/00* (2006.01)
*A61B 1/04* (2006.01)

(52) U.S. Cl.
CPC ...... *A61B 1/00059* (2013.01); *A61B 1/00006* (2013.01); *A61B 1/00009* (2013.01); *A61B 1/00039* (2013.01); *A61B 1/00045* (2013.01); *A61B 1/00055* (2013.01); *A61B 1/00105* (2013.01); *A61B 1/042* (2013.01); *A61B 1/0002* (2013.01); *A61B 1/00057* (2013.01); *A61B 1/00062* (2013.01); *A61B 2560/0475* (2013.01); *A61B 2562/08* (2013.01)

(58) Field of Classification Search
CPC ...... A61B 90/94; A61B 90/96; A61B 1/00062
See application file for complete search history.

(56) References Cited

U.S. PATENT DOCUMENTS

| | | | |
|---|---|---|---|
| 5,233,416 A | 8/1993 | Inoue | |
| 5,392,067 A * | 2/1995 | Konno | H04N 5/357 348/65 |
| 5,896,166 A | 4/1999 | D'Alfonso et al. | |
| 6,092,722 A | 7/2000 | Heinrichs et al. | |
| 6,293,911 B1 * | 9/2001 | Imaizumi | A61B 1/00009 600/160 |
| 6,638,212 B1 | 10/2003 | Oshima | |
| 6,712,756 B1 | 3/2004 | Kura et al. | |
| 6,770,027 B2 | 8/2004 | Banik et al. | |

(Continued)

FOREIGN PATENT DOCUMENTS

| JP | S56158632 | 12/1981 |
|---|---|---|
| JP | 6161841 | 7/2017 |

(Continued)

OTHER PUBLICATIONS

"Fundamentals of Bar Code Information Theory", by T. Pavlidis, J. Swartz and Y.P. Wang, IEEE Computer, Apr. 1990, pp. 74-86.

(Continued)

*Primary Examiner* — John P Leubecker
*Assistant Examiner* — Minqiao Huang
(74) *Attorney, Agent, or Firm* — Karish & Bjorgum, PC

(57) ABSTRACT

An endoscopic camera system has an endoscope having a field stop encoded with endoscope information; a camera head coupleable to the endoscope, the camera head generating image data including the endoscope information; and a camera control unit coupleable to the camera head to receive image data from the camera head; and wherein the camera control unit is configured to analyze the endoscope information to identify the endoscope coupled to the camera head.

25 Claims, 8 Drawing Sheets

(56) References Cited

U.S. PATENT DOCUMENTS

| | | |
|---|---|---|
| 7,282,026 B2 | 10/2007 | Ogawa |
| 7,289,139 B2 | 10/2007 | Amling et al. |
| 8,266,129 B2 | 9/2012 | Shimizu et al. |
| 8,373,748 B2 | 2/2013 | Pang et al. |
| 8,537,210 B2 | 9/2013 | Omori |
| 9,060,674 B2 | 6/2015 | Amling |
| 9,438,897 B2 | 9/2016 | Barreto et al. |
| 9,603,512 B2 | 3/2017 | Hoeg et al. |
| 10,350,001 B2* | 7/2019 | Collins .................. A61B 90/94 |
| 2004/0030221 A1 | 2/2004 | Ogawa |
| 2004/0186351 A1* | 9/2004 | Imaizumi ........... A61B 1/00009 600/160 |
| 2009/0124855 A1 | 5/2009 | Urakawa |
| 2010/0141744 A1 | 6/2010 | Amling et al. |
| 2015/0309284 A1* | 10/2015 | Kagawa ............. G02B 23/2453 348/76 |
| 2017/0007095 A1 | 1/2017 | Kutsuma et al. |
| 2018/0242828 A1* | 8/2018 | Shiga ............... H04N 5/232123 |
| 2019/0053693 A1 | 2/2019 | Koiso et al. |

FOREIGN PATENT DOCUMENTS

| | | |
|---|---|---|
| WO | 2016040131 | 3/2016 |
| WO | 2017072950 | 5/2017 |

OTHER PUBLICATIONS

"Waveform Recognition With Application to Bar Codes", by E. Joseph and T. Pavlidis, Proc. IEEE SMC Aug.1991, pp. 129-134.

"A Robust Software Barcode Reader Using the Hough Transform", by Ruben Muniz, et al., IEEE, Sep. 1999, pp. 313-319.

Annex to form PCT/ISA/206 Communication Relating to the Results of the Partial International Search—for PCT Application No. PCT/US2018/048322, dated Dec. 12, 2018, 13 pages.

International Search Report and Written Opinion, dated Apr. 10, 2019.

* cited by examiner

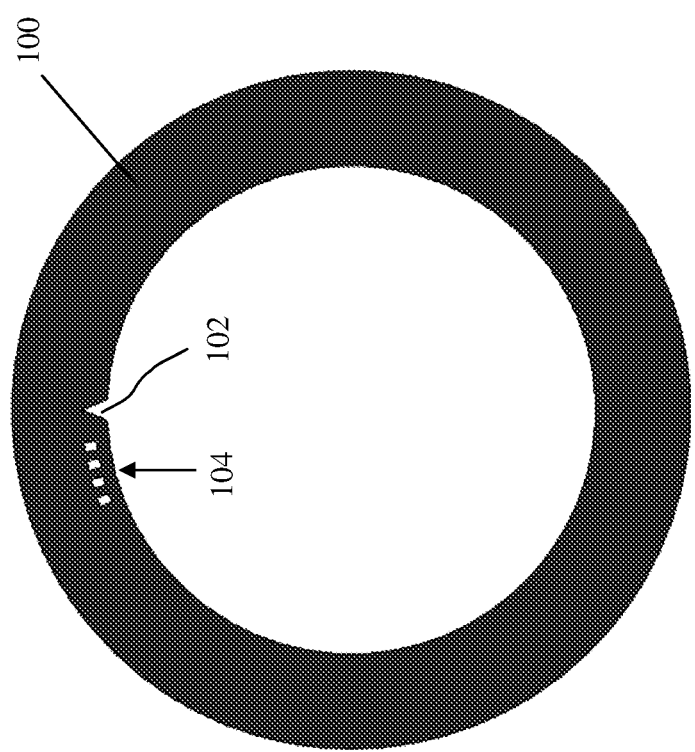
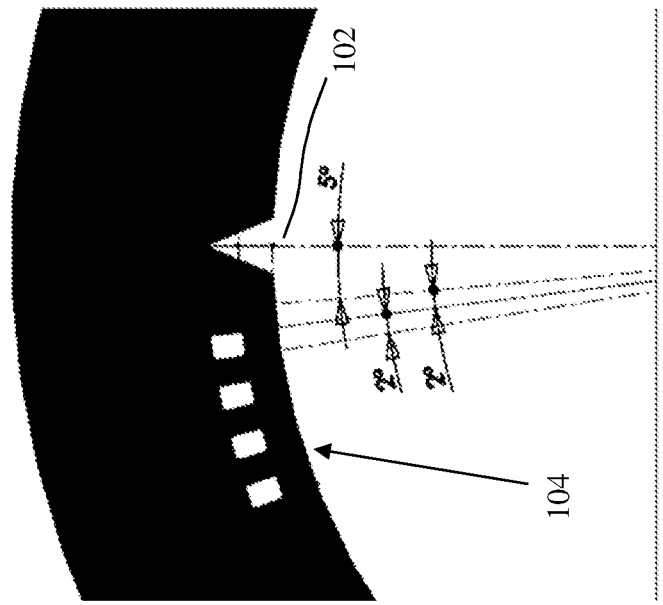
FIG. 7A
FIG. 7B

ENDOSCOPE FIELD STOP ENCODING SYSTEM AND METHOD

BACKGROUND

The present invention relates to devices used in endoscopic surgery and, more particularly, to endoscopic devices with field stop encoding allowing automatic identification of an endoscope that is coupled to an endoscopic video camera.

Endoscopic camera systems provide a surgeon with a view of an area of the body being worked on without the necessity of fully opening up the area, thereby allowing for less invasive surgical procedures. Generally, these devices consist of a camera head coupled to an endoscope and a camera control unit. Different endoscopes are used depending on the area of the body being worked on and the procedures being performed. Likewise, optimal camera settings are different depending on the endoscope being used, the area of the body being worked on and the procedures being performed. It would be desirable to have a system for automatically determining the endoscope being used for optimizing one or more settings for the display or processing of images that improves upon the prior art.

SUMMARY

The present disclosure relates to an endoscopic camera system, which is usable with multiple different endoscopes. A field stop of the endoscope is encoded with detectable endoscope information for customization of the camera system based on the endoscope being used.

In an exemplary embodiment, the endoscopic camera system has an endoscope having a field stop encoded with endoscope information; a camera head coupleable to the endoscope, the camera head generating image data including the endoscope information; and a camera control unit coupleable to the camera head to receive image data from the camera head; and wherein the camera control unit is configured to analyze the endoscope information to identify the endoscope coupled to the camera head. The endoscope information may include an endoscope type. Additionally, the endoscope information may include a unique endoscope identification number.

The system may be usable with more than one endoscope and the endoscope information in each of the plurality of endoscopes may have a same start feature and a same end feature. The field stop may be encoded with endoscope information using notches or slots having varying widths. The field stop may also be encoded with endoscope information using notches or slots having varying lengths. The field stop may be encoded with endoscope information at more than one location. Optionally, the field stop has a direction of view indicator and the camera control unit infers location of the direction of view indicator from the locations of the endoscope information.

The camera control unit may automatically adjust operational settings of the camera head in accordance with the endoscope coupled to the camera head. Optionally, the camera control unit automatically adjusts the operational settings of the camera control unit in accordance with the endoscope coupled to the camera head.

In a further exemplary embodiment of the present invention, the system has a memory coupled to the camera control unit and the camera control unit obtains endoscope usage information from the memory. The camera control unit may also track endoscope usage and send endoscope usage information to the memory.

In a further exemplary embodiment, the present invention is directed to a method of communicating endoscope information from an endoscope having a field stop to a camera head, and communicating endoscope information from the camera head to a camera control unit comprising the steps of: coupling the camera head to the endoscope; generating image data with the camera head including the endoscope information encoded in the field stop; transmitting the image data from the camera head to the camera control unit; and analyzing the image data from the camera head to identify the endoscope coupled to the camera head.

The method may also have the step of validating whether the endoscope is appropriate for use with the camera head. Optionally, the method has the step of storing endoscope usage information in a storage device. Optionally, the method has the step of modifying image data processing based upon the identified endoscope. Optionally, the method has the step of modifying image data display based upon the identified endoscope. Optionally, the method has the step of modifying a light setting based upon the identified endoscope.

The method may also have the step of comparing image data characteristics of the endoscope with saved image characteristics of an identified endoscope type. The method may also have the step of encoding endoscope information in the field stop. The step of encoding endoscope information in the field stop may include manufacturing holes, slots or notches of varying widths in the field stop and the step of analyzing the image data to identify the endoscope may include scanning the image data for contrast of pixels in a known image location.

In a further exemplary embodiment, the present invention is directed to an endoscope imaging system having an endoscope with a field stop encoded with endoscope information. The system may also have a camera head with an image sensor generating image data including the endoscope information from the field stop. The system may also have a camera control unit receiving image data from the camera head, the camera control unit being configured to analyze the image data to identify the endoscope. Optionally, the endoscope information is encoded as a plurality of holes, slots or notches in the field stop. Optionally, the endoscope information is encoded in a plurality of locations in the field stop. Optionally, the encoded information is digitally removed from an image presented to a user.

These and other features are described below.

BRIEF DESCRIPTION OF THE DRAWINGS

The features, aspects and advantages of the present invention will become better understood with regard to the following description, appended claims and accompanying figures wherein:

FIGS. 7A and 7B illustrate a field stop with encoded endoscope information according to a fifth embodiment of the present invention.

DETAILED DESCRIPTION

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

Figure 1:
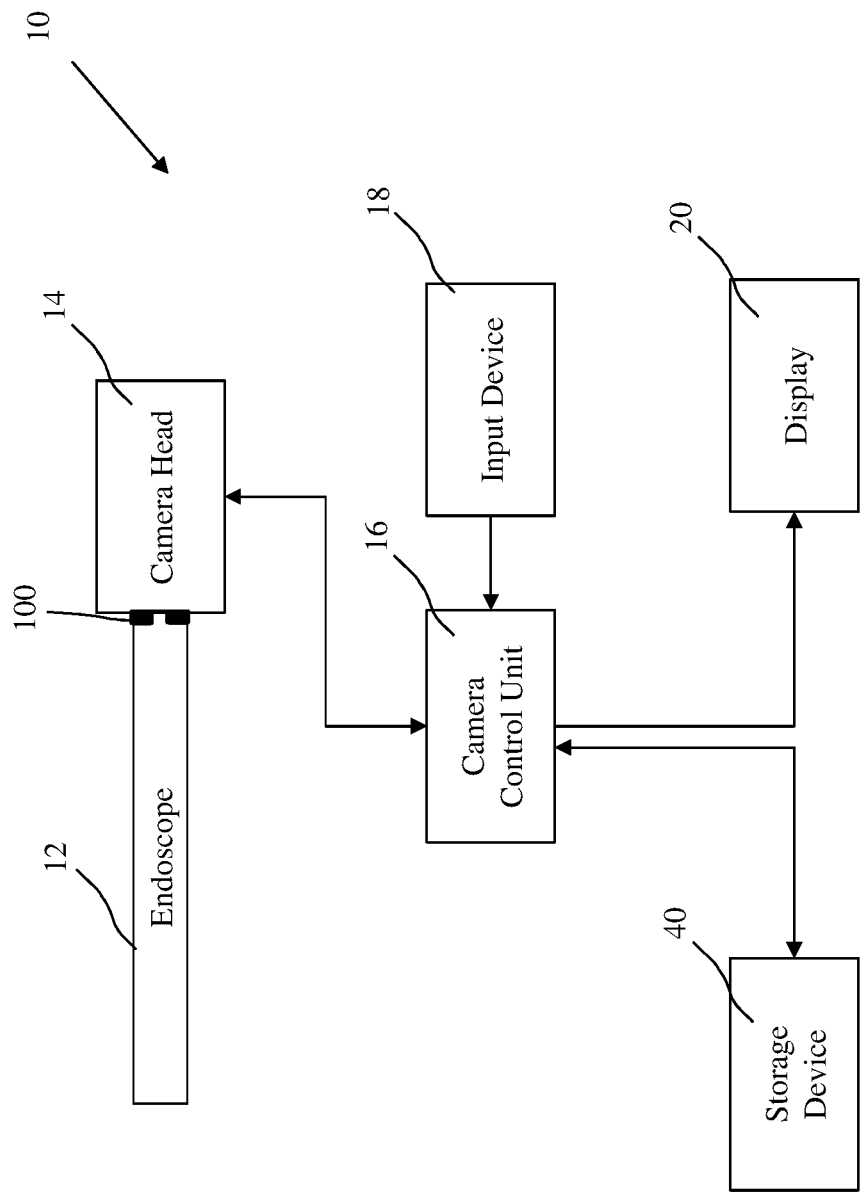
FIG. 1 is a schematic diagram of a camera system according to an embodiment of the present invention.
Figure 2:
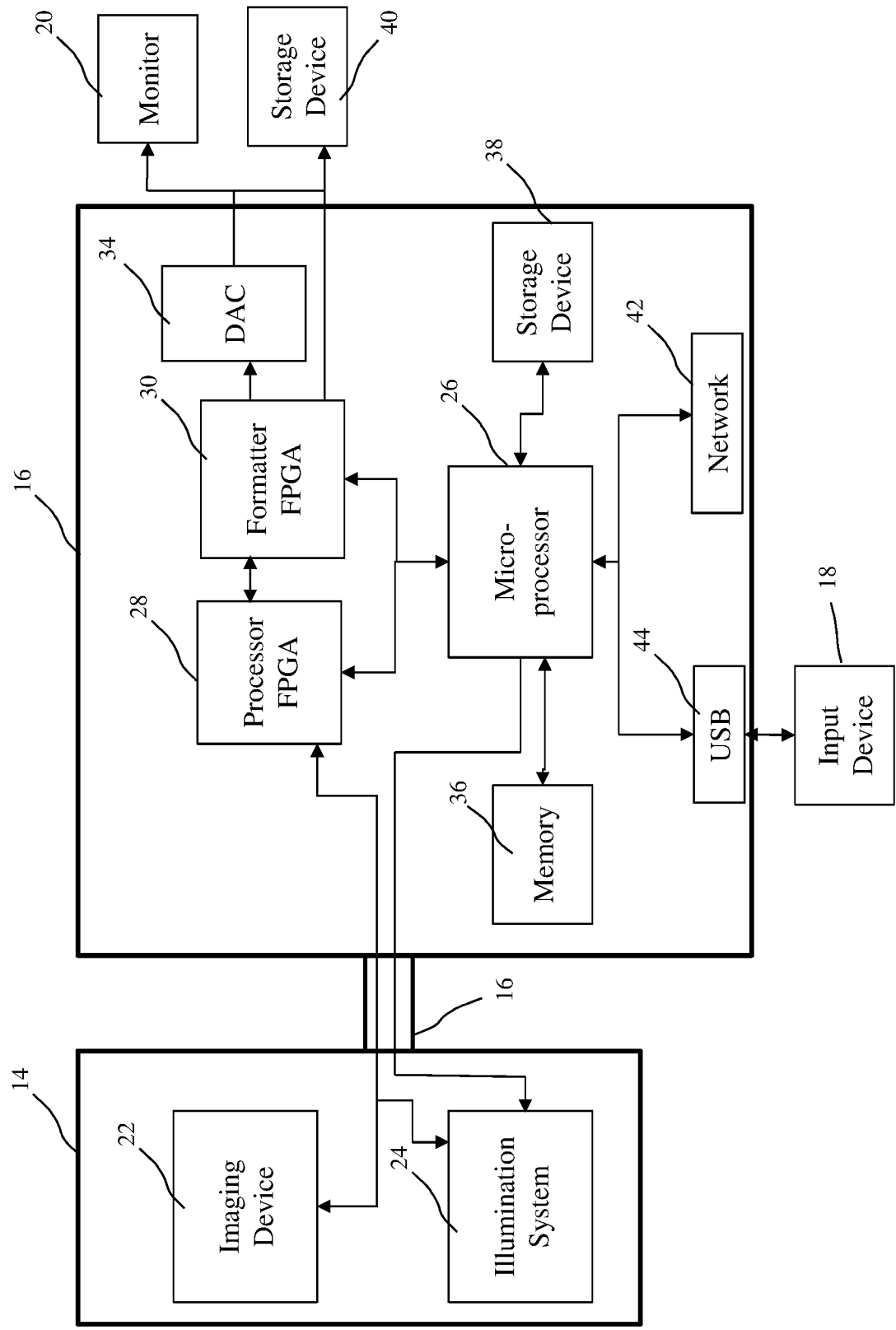
FIG. 2 is a schematic diagram of a camera control unit and camera head usable in the camera system of FIG. 1.

With reference to FIGS. 1 and 2, an endoscopic camera system 10 according to an embodiment of the present invention has at least one endoscope 12 connectable to a camera head 14. The camera head 14 is connectable to a camera control unit 16 ("CCU"). The camera head 14 and camera control unit 16 may be connected via wire or wirelessly. The camera control unit 16 is also connectable to at least one input device 18 such as a mouse, keyboard, touchpad, or touchscreen monitor. Additionally, the camera control unit is connectable to a display 20.

As shown in FIG. 2, the camera head 14 has an imaging device 22 which may include NTSC/PAL, single chip, three chip, standard definition, high definition, ultra high definition, CCD and CMOS devices. The camera head may also have an illumination system 24. The camera head 12 may also have memory for storing camera data, camera control unit processing data or other information. The camera head 12 may also have a user input means such as buttons to control aspects of image capture.

As shown in FIG. 2, the camera control unit 16 contains a microprocessor 26 for interfacing with user input devices 18, a signal processing circuit 28, a signal formatting circuit 30, digital to analog converters 34 and memory 36. The camera control unit 16 runs program applications providing for a variety of capabilities. For example, the camera control unit 16 may provide for a live feed of the image generated by the camera head 14 to be displayed through the display 20. Additionally, the camera control unit 16 may provide image capture functionality allowing for images generated by the camera head 14 to be saved to a storage device, such as an internal storage device 38 or a storage device 40 external to the camera control unit. The captured images may be annotated and/or edited and displayed through the display 20.

In an embodiment, the camera control unit 16 also has at least one network interface 42 which may be a wired interface such as Ethernet, or a wireless network connection that allows for the camera control unit to access a network. Optionally, the network interface 42 allows the camera control unit 16 to access the Internet and servers for storing and processing information.

In an embodiment, the external storage device 40 may be, for example, a flash memory storage device or a hard disk storage device, and may be connected to the camera control unit 14 through a USB connection 44 or firewire connection (not shown). In an embodiment, a program application for the camera control unit, or data relevant to a particular patient, surgeon or endoscope, is stored on the external storage device 40 and may be used to quickly configure the camera control unit for future sessions. Preferably, the camera control unit 16 can save images and video in different formats and to different places (e.g. internal memory, an external memory, or to a remote location over the Internet). Additionally, the external storage device 40 may be a server and may be connected to the camera control unit the network interface 42.

With reference to FIGS. 3 and 4, the endoscope 12 has a field stop 100 to control unwanted stray light. The field stop 12 produces a round aperture in the field of view. Also included in the field stop 12 is a visual orientation marker 102 to help a user track a direction of view. The visual orientation marker 102 may be aligned with a light post (not shown) connected to the endoscope. The field stop 100 may be a small black metal mask with an aperture placed at a specific location in the optical path on the inside of the endoscope 12. The visual orientation marker 102 may be, for example, a small triangular notch at the edge of the aperture.

In an embodiment of the present invention, information features 104 for specific endoscopes are placed in an inner edge of the field stop. The information features 104 may be recognized by an image processing algorithm that scans an image received from a camera head to identify the aperture of the field stop, using the contrast of the pixels and their approximate known location.

A ring of pixels just outside the field stop aperture (in the mask) is extracted. The ring of pixels is then analyzed to locate the orientation notch as well as the information features 104. Optionally, in an embodiment, the information features 104 have start features 106 and end features 108 that are the same for each endoscope so that an algorithm can determine where endoscope data 110 begins and ends.

In an embodiment, the endoscope data 110 is encoded between the start and stop features 106, 108. The endoscope data may be encoded using, for example, a narrow notch or a wide notch constituting "bits" of data. A "bit" may also be, for example, a short notch or a long notch. Although the present specification refers to use of notches, it will be understood that slots, holes or other detectable shapes may be used to encode information into the field stop. In additional embodiments, the encoding may be done with other optically detectable means, such as, for example, a colored marking or a fluorescent phosphor.

The bits are interpreted as a 1 or a 0 as effectively a binary code. In an embodiment, the endoscope data 110 is between about 4 and about 24 "bits" between the start and stop features 106, 108. In a more preferred embodiment, the endoscope data 110 is about 8 "bits" between the start and stop feature 106, 108. Although described herein as a binary system, it is also possible that shapes may be used to encode more than two values. For example, a notch may have three or four different lengths or widths and may thereby be used to encode four or five different values. This allows fewer notches to encode more information.

In a preferred embodiment, two or more copies of the information features 104 are provided at different positions on the field stop 100 so that endoscope information may still be obtained even if one set of information features 104 are oriented off an edge of a video image. Moreover, if the locations of the multiple copies of the information features 104 is known, then that information may be used to infer the location of the orientation notch 102.

Figure 3B:
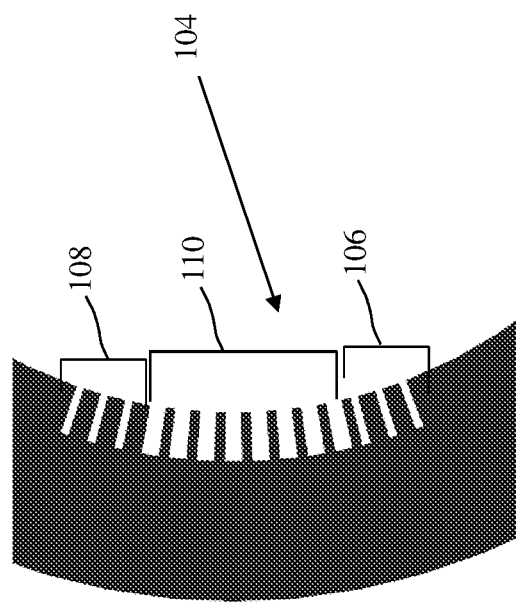
FIGS. 3A and 3B illustrate field stops with encoded endoscope information according to a first embodiment of the present invention.
Figure 3A:
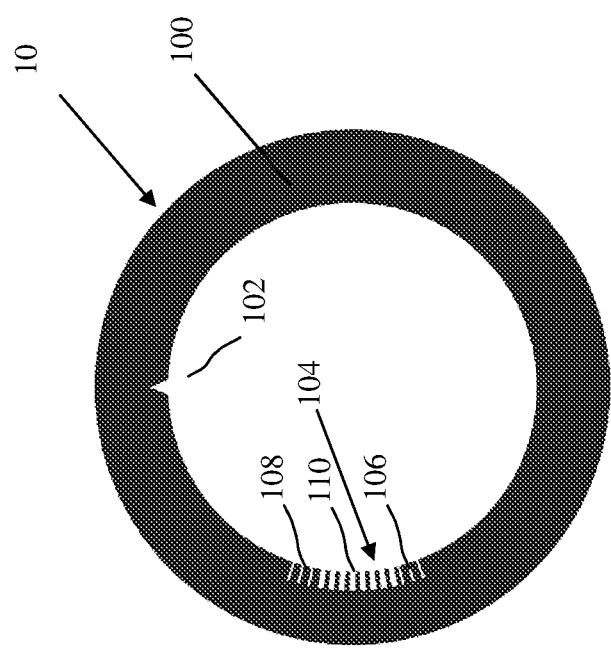

A field stop aperture according to a first exemplary embodiment of the present invention is shown in FIGS. 3A and 3B. In this embodiment, a notch of one degree in width is considered to be a value of zero and a notch of two degrees in width is considered to be a value of one. A bit is oriented every three degrees with each bit being separated by one to two degrees of field stop. In this embodiment, the start feature 106 constitutes three zero bits and the end feature 108 constitutes three zero bits. In between the start feature 106 and the end feature 108, are eight notches for endoscope data (shown as ones). The eight notches for endoscope data may be used to identify 256 different types of endoscopes. In this exemplary embodiment, the depth of the notches equal the depth of the orientation notch 102 which may allow the algorithm used to detect the orientation notch to detect the identifying features.

Figure 4A:
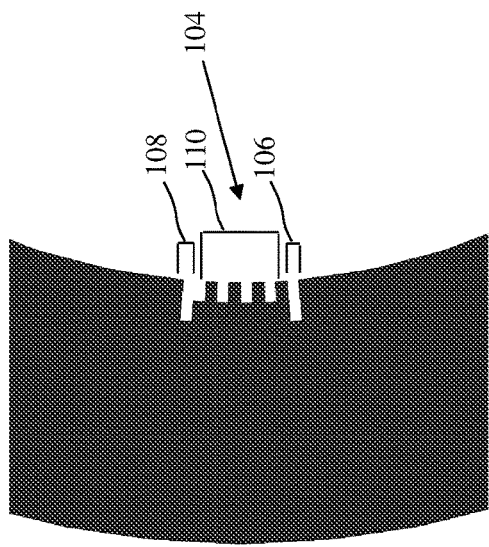
FIGS. 4A, 4B, 4C and 4D illustrate field stops with encoded endoscope information according to a second embodiment of the present invention.
Figure 4B:
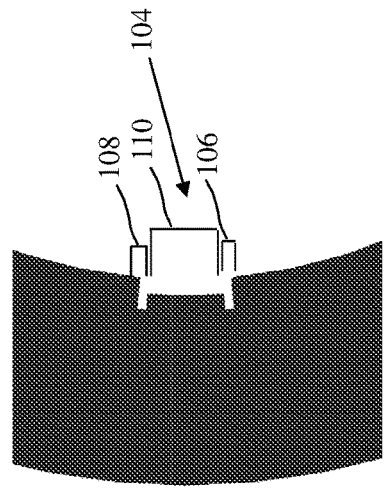
Figure 4C:
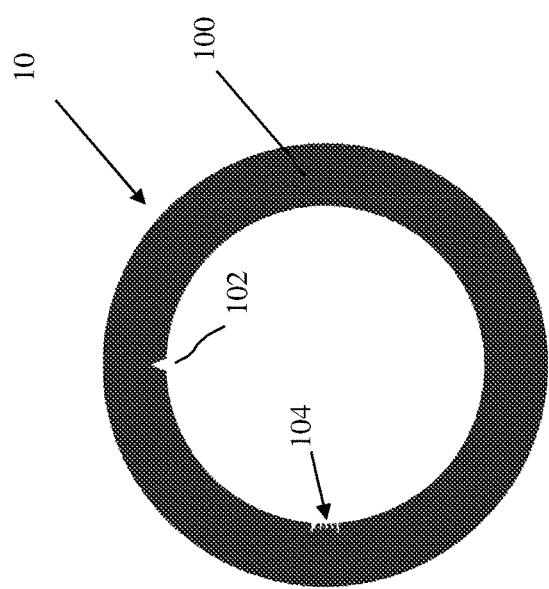
Figure 4D:
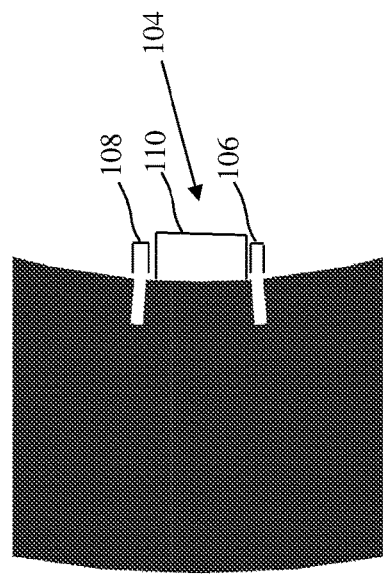

A field stop aperture according to a second exemplary embodiment of the present invention is shown in FIGS. 4A through 4D. In this embodiment, the presence of a notch of one degree is considered to be a value of zero and the lack of a notch is considered to be a value of one and there is no separation between bits. Optionally, the presence of a notch may be considered to be a value of one and the lack of a notch may be considered a value of zero. In this embodiment, the start feature 106 and the end feature 108 each constitute one long notch having a depth equal to the depth of the orientation notch 102. In between the start feature 106 and the end feature 108, are up to eight notches for endoscope data (shown as ones). The eight notches for endoscope data may be used to identify 256 different types of endoscopes. In this exemplary embodiment, the depth of the endoscope data notches equals one half of the depth of the orientation notch 102. FIG. 4B shows a field stop with endoscope data encoded with eight alternating ones and zeros. FIG. 4C shows a field stop encoded with all endoscope data bits encoding a one. FIG. 4D shows a field stop encoded with all endoscope data bits encoding a zero.

Figure 5B:
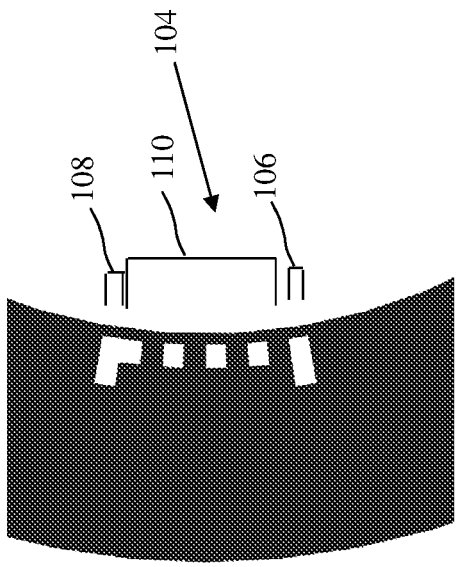
FIGS. 5A, 5B, 5C and 5D illustrate field stops with encoded endoscope information according to a third embodiment of the present invention.
Figure 5D:
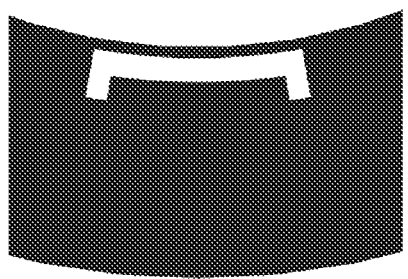
Figure 5A:
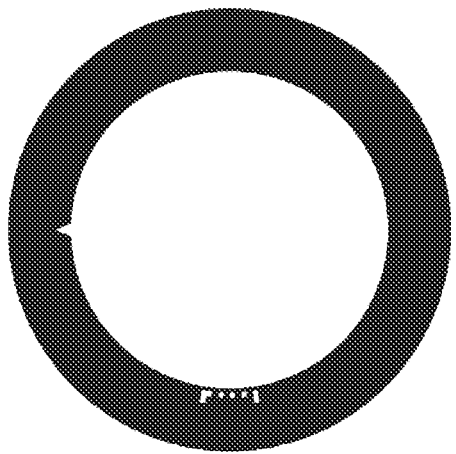
Figure 5C:
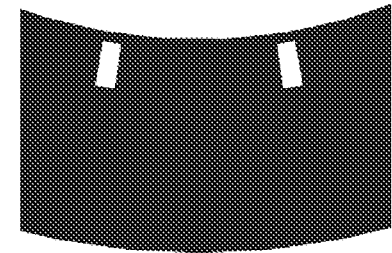

A field stop aperture according to a third exemplary embodiment of the present invention is shown in FIGS. 5A through 5D. In this embodiment, the presence of a notch of two degrees is considered to be a value of zero, the lack of a notch is considered to be a value of one and there is no separation between bits. In this embodiment, the start feature 106 and the end feature 108 each constitute one long notch having a depth equal to the depth of the orientation notch 102. In between the start feature 106 and the end feature 108, are up to eight notches for endoscope data (shown as ones). The eight notches for endoscope data may be used to identify 256 different types of endoscopes. In this exemplary embodiment, the depth of the endoscope data notches equal one half of the depth of the orientation notch 102. However, this embodiment differs from the second exemplary embodiment in that the notches do not interrupt the inner diameter edge of the field stop. By not interrupting the inner diameter edge, the information features 104 are less likely to confuse an algorithm used for finding the orientation notch 102. FIG. 5B shows a field stop encoded with eight endoscope data bits of alternating ones and zeros. FIG. 5C shows a field stop encoded with eight endoscope data bits all encoding a one. FIG. 5D shows a field stop encoded with eight endoscope data bits all encoding a zero.

Figure 6:
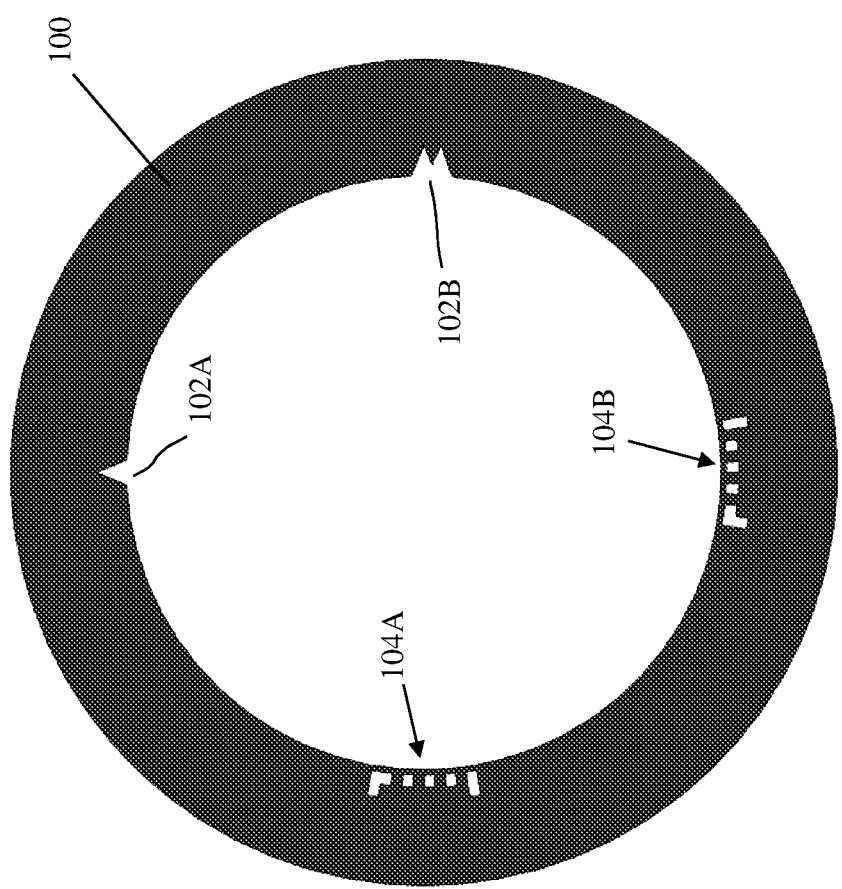
FIG. 6 illustrates a field stop with encoded endoscope information according to a fourth embodiment of the present invention.

A field stop aperture according to a fourth exemplary embodiment of the present invention is shown in FIG. 6. In this embodiment, the field stop aperture is encoded with two orientation notches 102A and 102B 90 degrees apart. Additionally, the field stop aperture is encoded with two of the same information features 104A and 104B positioned 90 degrees apart. In an additional embodiment, the endoscope data bits in each of the information features are comple-ments of each other. In additional embodiments, any number of orientation notches and information features 104 can be placed in the field stop.

A field stop aperture according to a fifth exemplary embodiment of the present invention is shown in FIGS. 7A and 7B. In this embodiment, the presence of a notch of two degrees is considered to be a value of zero, the lack of a notch is considered to be a value of one and there is no separation between bits. In this embodiment, there are no start features or end features and the depth of the endoscope data notches equal one half of the depth of the orientation notch 102. In this embodiment, the endoscope data 110 is positioned a predetermined distance (five degrees) from the orientation notch 102. By positioning the endoscope data 100 a predetermined distance from the orientation notch, an algorithm for obtaining the endoscope information does not need to use start features or end features to locate the data.

Figure 8:
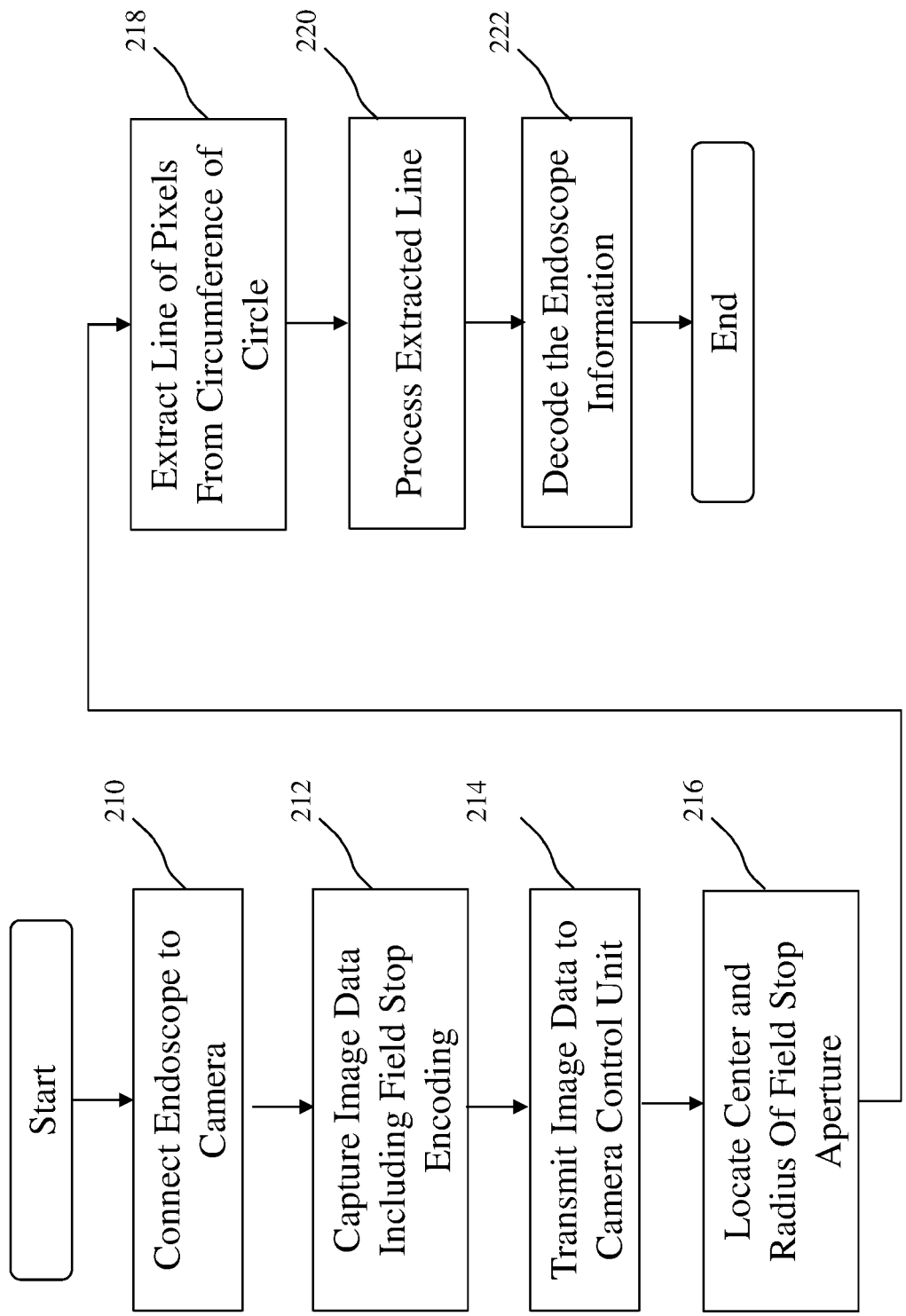
FIG. 8 is a block diagram showing an example of how encoded endoscope information is obtained according to an embodiment of the present invention.

As shown in FIG. 8, the present invention is also directed to a method for extracting endoscope information from a field stop image. An endoscope is initially coupled to a camera head, box 210. The camera head then captures image data, including endoscope information encoded in the field stop, box 212. Preferably, an image is captured during a white balance operation. The white balance operation may be initiated automatically when an endoscope is connected to a camera head. Alternatively, a user may manually initiate a white balance. Optionally, upon connection of an endoscope to the camera head, the camera control unit causes display of a message instructing the user to initiate a white balance operation. Capturing a screen image during a white balance operation ensures that the image is predominantly white, correctly exposed and that the image fills the entire endoscope field of view. The image data is transmitted to a camera control unit, box 214.

Optionally, the captured image is converted from RGB to gray scale. Removing color simplifies later processing. Optionally, a smoothing filter is applied to remove noise. The smoothing filter cutoff is chosen so as to avoid damaging detail of the identification information while removing unwanted noise. A Gaussian filter can be implemented as a separable low pass with sharp cutoff to remove unwanted noise. Image contrast may be increased to accentuate the black and white differences in the image.

A Hough Circle Transform is performed to locate the center ($x_{center}$, $y_{center}$) and radius (r) of the field stop circle, box 216. A one dimensional line of pixels is extracted from the circumference of the concentric circle with radius r+x where x is chosen so that the line fully intersects the code features in the field stop image, box 218. The one dimensional line of pixels is then processed using a standard linear barcode decoding algorithm, box 220. Standard barcode decoding algorithms may be found in, for example, T. Pavlidis, J. Swartz, and Y. P. Wang, "Fundamentals of bar code information theory," IEEE Computer, pp. 74-86, April 1990, E. Joseph and T. Pavlidis, "Waveform recognition with applications to bar codes," in Proc. IEEE SMC 1991 Con&, 1991, pp. 129-134, R. Muniz, L. Junco and A. Otero, "A robust software barcode reader using the Hough transform," International Conference on Information Intelligence and Systems, Bethesda, Md., USA, pp. 313-319, November 1999, the entire contents of each of which are incorporated herein by reference in their entirety. The endoscope information is then decoded, box 222. The endoscope information may include, for example, a model number, a serial number, a field of view and an angle of view.

Once endoscope information is obtained, the endoscope information can be used to reference image processing, light settings, or display settings in a memory in the camera control unit or in a memory accessible by the camera control unit. The image processing, light settings, or display settings may be automatically implemented by the camera control unit. Also, for example, the image for a particular endoscope may be automatically magnified to a predetermined magnification. Also, for example, the operational settings of the camera head may be automatically adjusted for the specific endoscope. Also, for example, optimal light source settings may be automatically selected for the particular endoscope. Endoscope information can also be used to prevent the use of incompatible endoscopes. For example, if a scope is used that is not validated for use with a given camera system, the camera control unit 16 may cause a warning to be displayed to a user on the display 20.

Additionally, the camera system can record and present usage statistics on which endoscopes are used, with which surgeries, and for how long. This data may be stored in a storage accessible to different camera control units so that the data may be updated when a particular endoscope is used in different locations with different camera heads and camera control units. This data can help surgeons keep records of which endoscopes were used in each procedure. Reliability of endoscopes can be more accurately tracked. Manufacturing, sales, and design may benefit from the data to make the most often used products, rather than relying on sales history.

Endoscope usage information is advantageous because usage time may affect the reliability and health of an endoscope. Once an endoscope is identified, target calibration can be used to gauge the health of the endoscope. For example, optimal light and exposure settings for a given type of endoscope may be compared with light and exposure settings used with the actual endoscope to determine whether the endoscope is functioning properly. The data may also be used to determine the health of different camera heads. For example, if the same endoscope is used with different camera heads and the usage requires very different light and exposure settings, then investigation of the camera heads may be warranted.

The information features 104 may be digitally removed from the image prior to presenting the image to a user and prior to archiving of the image. Removal of the encoded information features 104 from the image may be advantageous to avoid confusing a user.

The present invention is advantageous, because while the method requires physical modification of the field stop, the invention does not require the addition of any components nor direct communication of identification information between an endoscope and a camera head or camera control unit. Moreover, each endoscope may be encoded with a specific identifier so that information about that specific endoscope may be tracked.

There is disclosed in the above description and the drawings, a surgical imaging system and method for processing surgical images that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An endoscopic camera system comprising:
   an endoscope having a field stop encoded with endoscope information using at least one of: a plurality of holes, a plurality of notches, and a plurality of slots;
   a camera head coupleable to the endoscope, the camera head generating image data including the endoscope information; and
   a camera control unit coupleable to the camera head to receive image data from the camera head; and
   wherein the camera control unit is configured to analyze the endoscope information to identify the endoscope coupled to the camera head.

2. The endoscopic camera system of claim 1 wherein the endoscope information comprises an endoscope type.

3. The endoscopic camera system of claim 1 wherein the endoscope information comprises at a unique endoscope identification number.

4. The endoscopic camera system of claim 1 wherein a width of the holes, notches and slots can be varied.

5. The endoscopic camera system of claim 1 wherein a length of the holes, notches and slots can be varied.

6. The endoscopic camera system of claim 1 wherein the camera control unit automatically adjusts operational settings of the camera head in accordance with the endoscope coupled to the camera head.

7. The endoscopic camera system of claim 1 wherein the camera control unit automatically adjusts the operational settings of the camera control unit in accordance with the endoscope coupled to the camera head.

8. The endoscopic camera system of claim 1 further comprising a memory coupled to the camera control unit and wherein the camera control unit obtains endoscope usage information from the memory.

9. The endoscopic camera system of claim 8 wherein the camera control unit tracks endoscope usage and sends endoscope usage information to the memory.

10. The endoscopic camera system of claim 1 wherein the field stop is encoded with endoscope information at a plurality of locations.

11. The endoscopic camera system of claim 10 wherein the field stop further comprises a direction of view indicator and wherein the camera control unit infers location of the direction of view indicator from the locations of the endoscope information.

12. A method of communicating endoscope information from an endoscope having a field stop to a camera head, and communicating endoscope information from the camera head to a camera control unit comprising the steps of:
    coupling the camera head to the endoscope;
    generating image data with the camera head including the endoscope information encoded in the field stop with at least one of: a plurality of holes, a plurality of notches and a plurality of slots;
    transmitting the image data from the camera head to the camera control unit; and
    analyzing the image data from the camera head to identify the endoscope information encoded in the field stop to identify the endoscope coupled to the camera head.

13. The method of claim 12 further comprising a step of validating whether the endoscope is appropriate for use with the camera head.

14. The method of claim 12 further comprising a step of storing endoscope usage information in a storage device.

15. The method of claim 12 further comprising a step of modifying image data processing based upon the identified endoscope.

16. The method of claim 12 further comprising a step of modifying image data display based upon the identified endoscope.

17. The method of claim 12 further comprising a step of modifying a light setting based upon the identified endoscope.

18. The method of claim 12 further comprising a step of comparing image data characteristics of the endoscope with saved image characteristics of an identified endoscope type.

19. The method of claim 12 further comprising a step of encoding endoscope information in the field stop.

20. The method of claim 19 wherein the step of encoding endoscope information in the field stop further comprising manufacturing a plurality of holes, slots or notches of varying widths in the field stop and the step of analyzing the image data to identify the endoscope further comprises scanning the image data for contrast of pixels in a known image location.

21. The method of claim 12 wherein the method further comprises a step of removing the encoded endoscope information from the image data.

22. An endoscope imaging system comprising an endoscope having a field stop encoded with endoscope information using at least one of: a plurality of holes, a plurality of notches, and a plurality of slots.

23. The endoscope imaging system of claim 22 further comprising a camera head comprising an image sensor generating image data including the endoscope information from the field stop.

24. The endoscope imaging system of claim 23 further comprising a camera control unit receiving image data from the camera head, the camera control unit being configured to analyze the image data to identify the endoscope.

25. The endoscope imaging system of claim 22 wherein the endoscope information is encoded in a plurality of locations in the field stop.

* * * * *